US006261784B1

(12) United States Patent
Nadeau et al.

(10) Patent No.: US 6,261,784 B1
(45) Date of Patent: *Jul. 17, 2001

(54) DETECTION OF NUCLEIC ACIDS BY STRAND DISPLACEMENT

(75) Inventors: James G. Nadeau, Chapel Hill; Helen V. Hsieh, Durham; J. Bruce Pitner, Durham; C. Preston Linn, Durham, all of NC (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/599,164

(22) Filed: Jun. 22, 2000

Related U.S. Application Data

(63) Continuation of application No. 09/235,583, filed on Jan. 22, 1999, now Pat. No. 6,130,047, which is a continuation of application No. 08/933,749, filed on Sep. 23, 1997, now Pat. No. 5,935,791.

(51) Int. Cl.[7] ............................... C12Q 1/68; C12P 19/34

(52) U.S. Cl. ........................ 435/6; 435/91.1; 435/91.2; 536/23.1; 536/24.3; 536/24.31; 536/24.32

(58) Field of Search ........................ 435/91.1, 6, 91.2; 536/23.1, 24.3, 24.31, 24.32

(56) References Cited

U.S. PATENT DOCUMENTS

| 5,270,184 | 12/1993 | Walker et al. . |
| 5,348,853 | 9/1994 | Wang et al. . |
| 5,451,503 | 9/1995 | Hogan et al. . |

(List continued on next page.)

FOREIGN PATENT DOCUMENTS

| 0 232 967 B1 | 4/1993 | (EP) . |
| 5-15439 | 3/1993 | (JP) . |
| WO 96/21144 | 7/1996 | (WO) . |

OTHER PUBLICATIONS

Ellwood, et al., Strand Displacement Applied to Assays with Nucleic Acid Probes, Clin. Chem., 32/9, 1631–1636 (1986).
Ghosh, et al., Real Time Kinetics of Restriction Endonuclease Cleavage Monitored by Fluorescence Resonance Engergy Transfer, Nucleic Acids Research, 1994, vol. 22, No. 15 3155–59.
Lee, et al., A Fluorometric Assay for DNA Cleavage Reactions Characterized with BamHI Restriction Endonuclease, Analytical Biochemistry 220, 377–383, 1994.
Lee, et al., Allelic Discrimination by Nick–translation PCR Fluorogenic Probes, Nucleic Acids Research, 1993, vol. 21, No. 16 3761–66.
Morrison, Detection of Energy Transfer and Fluorescence Quenching, Nonisotopic DNA Probe Techniques, 1992, 311.

*Primary Examiner*—Kenneth R. Horlick
(74) *Attorney, Agent, or Firm*—David W. Highet

(57) ABSTRACT

Detector nucleic acids are employed for detection of nucleic acid target sequences by fluorescence quenching mechanisms. The detector nucleic acid comprises at least two oligonucleotides and is partially single-stranded and partially double-stranded. One of the two dyes of a donor/acceptor dye pair is linked to the first oligonucleotide and the other is linked to a second oligonucleotide such that they are in close spatial proximity when the first and second oligonucleotides are base-paired and donor fluorescence is quenched. A single second oligonucleotide may be hybridized to the first oligonucleotide or multiple second oligonucleotides may be hybridized to the first oligonucleotide and to each other, forming a junction structure comprising multiple donor/acceptor dye pairs. The detector oligonucleotide retains its partially single-stranded and partially double-stranded conformation in the absence of target. In the presence of target, however, the second oligonucleotide(s) of the detector nucleic acid is/are completely or partially displaced from the first, increasing the distance between the donor and acceptor dyes and causing a change in fluorescence which may be detected as an indication of the presence of the target sequence.

12 Claims, 4 Drawing Sheets

U.S. PATENT DOCUMENTS

| | | |
|---|---|---|
| 5,455,166 | 10/1995 | Walker . |
| 5,514,546 | 5/1996 | Kool . |
| 5,547,861 | 8/1996 | Nadeau et al. . |
| 5,607,834 | 3/1997 | Bagwell . |
| 5,627,032 | 5/1997 | Ulanovsky . |
| 5,629,153 * | 5/1997 | Urdea ................ 435/6 |
| 5,691,145 | 11/1997 | Pitner et al. . |
| 5,712,386 | 1/1998 | Wang et al. . |

* cited by examiner

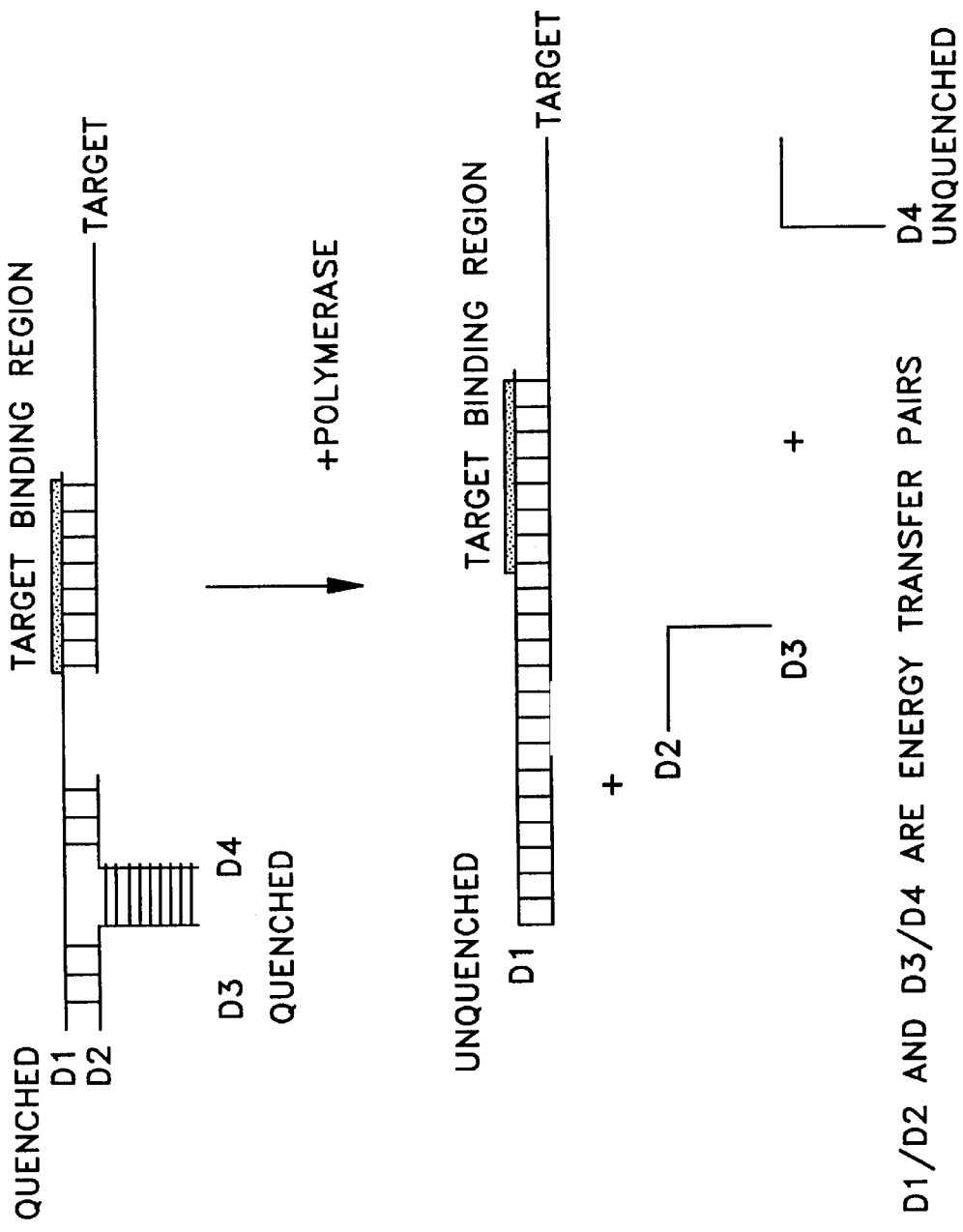

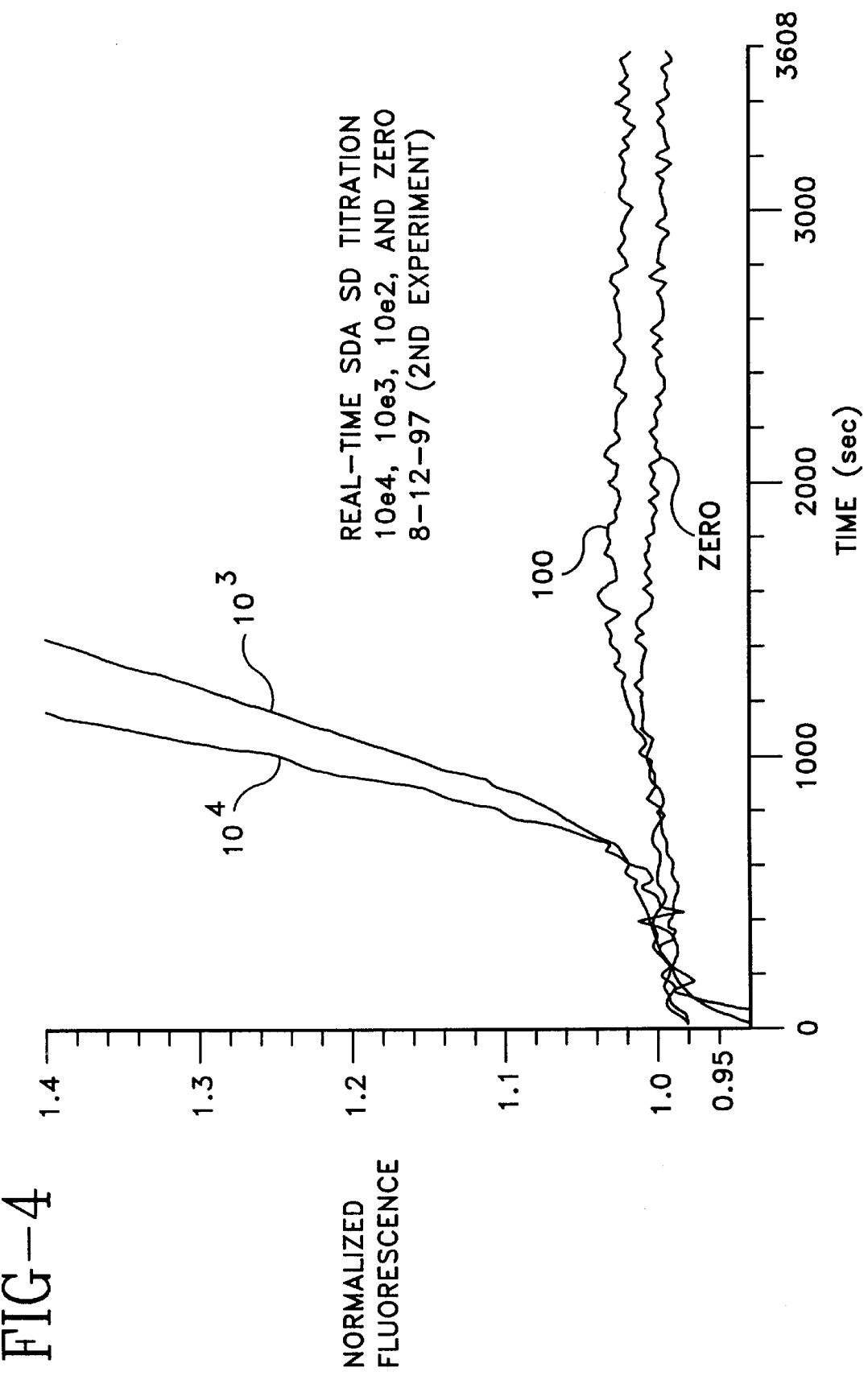

DETECTION OF NUCLEIC ACIDS BY STRAND DISPLACEMENT

This is a continuation of prior application Ser. No. 09/235,583, filed Jan. 22, 1999, U.S. Pat. No. 6,130,047, which is a continuation of Ser. No. 08/933,749, filed Sep. 23, 1997, now issued as U.S. Pat. No. 5,935,791.

FIELD OF THE INVENTION

The invention relates to methods for detecting nucleic acid target sequences, and in particular to detection methods employing fluorescence quenching.

BACKGROUND OF THE INVENTION

Sequence-specific hybridization of oligonucleotide probes has long been used as a means for detecting and identifying selected nucleotide sequences, and labeling of such probes with fluorescent labels has provided a relatively sensitive, nonradioactive means for facilitating detection of probe hybridization. Recently developed detection methods employ the process of fluorescence energy transfer (FET) rather than direct detection of fluorescence intensity for detection of probe hybridization. Fluorescence energy transfer occurs between a donor fluorophore and an acceptor dye (which may or may not be a fluorophore) when the absorption spectrum of one (the acceptor) overlaps the emission spectrum of the other (the donor) and the two dyes are in close proximity. Dyes with these properties are referred to as donor/acceptor dye pairs or energy transfer dye pairs. The excited-state energy of the donor fluorophore is transferred by a resonance dipole-induced dipole interaction to the neighboring acceptor. This results in quenching of donor fluorescence. In some cases, if the acceptor is also a fluorophore, the intensity of its fluorescence may be enhanced. The efficiency of energy transfer is highly dependent on the distance between the donor and acceptor, and equations predicting these relationships have been developed by Förster (1948. *Ann. Phys.* 2, 55–75). The distance between donor and acceptor dyes at which energy transfer efficiency is 50% is referred to as the Förster distance ($R_O$). Other mechanisms of fluorescence quenching are also known including, for example, charge transfer and collisional quenching.

Energy transfer and other mechanisms which rely on the interaction of two dyes in close proximity to produce quenching are an attractive means for detecting or identifying nucleotide sequences, as such assays may be conducted in homogeneous formats. Homogeneous assay formats are simpler than conventional probe hybridization assays which rely on detection of the fluorescence of a single fluorophore label, as heterogeneous assays generally require additional steps to separate hybridized label from free label. Typically, FET and related methods have relied upon monitoring a change in the fluorescence properties of one or both dye labels when they are brought together by the hybridization of two complementary oligonucleotides. In this format, the change in fluorescence properties may be measured as a change in the amount of energy transfer or as a change in the amount of fluorescence quenching, typically indicated as an increase in the fluorescence intensity of one of the dyes. In this way, the nucleotide sequence of interest may be detected without separation of unhybridized and hybridized oligonucleotides. The hybridization may occur between two separate complementary oligonucleotides, one of which is labeled with the donor fluorophore and one of which is labeled with the acceptor. In double-stranded form there is decreased donor fluorescence (increased quenching) and/or increased energy transfer as compared to the single-stranded oligonucleotides. Several formats for FET hybridization assays are reviewed in *Nonisotopic DNA Probe Techniques* (1992. Academic Press, Inc., pgs. 311–352).

Alternatively, the donor and acceptor may be linked to a single oligonucleotide such that there is a detectable difference in the fluorescence properties of one or both when the oligonucleotide is unhybridized vs. when it is hybridized to its complementary sequence. In this format, donor fluorescence is typically increased and energy transfer/quenching are decreased when the oligonucleotide is hybridized. For example, a self-complementary oligonucleotide labeled at each end may form a hairpin which brings the two fluorophores (i.e., the 5' and 3' ends) into close proximity where energy transfer and quenching can occur. Hybridization of the self-complementary oligonucleotide to its complement on a second oligonucleotide disrupts the hairpin and increases the distance between the two dyes, thus reducing quenching. A disadvantage of the hairpin structure is that it is very stable and conversion to the unquenched, hybridized form is often slow and only moderately favored, resulting in generally poor performance. Tyagi and Kramer (1996. *Nature Biotech.* 14, 303–308) describe a hairpin labeled as described above with a detector sequence in the loop between the self-complementary arms of the hairpin which form the stem. The base-paired stem must melt in order for the detector sequence to hybridize to the target and cause a reduction in quenching. A "double hairpin" probe and methods of using it are described by B. Bagwell, et al. (1994. *Nucl. Acids Res.* 22, 2424–2425; U.S. Pat. No. 5,607,834). These structures contain the target binding sequence within the hairpin and therefore involve competitive hybridization between the target and the self-complementary sequences of the hairpin. Bagwell solves the problem of unfavorable hybridization kinetics by destabilizing the hairpin with mismatches, thus favoring hybridization to the target.

Homogeneous methods employing energy transfer or other mechanisms of fluorescence quenching for detection of nucleic acid amplification have also been described. R. Higuchi, et al. (1992. *Biotechnology* 10, 413–417) disclose methods for detecting DNA amplification in real-time by monitoring increased fluorescence of ethidium bromide as it binds to double-stranded DNA. The sensitivity of this method is limited because binding of the ethidium bromide is not target specific and background amplification products are also detected. L. G. Lee, et al. (1993. *Nuc. Acids Res.* 21, 3761–3766) disclose a real-time detection method in which a doubly-labeled detector probe is cleaved in a target amplification-specific manner during PCR. The detector probe is hybridized downstream of the amplification primer so that the 5'-3' exonuclease activity of Taq polymerase digests the detector probe, separating two fluorescent dyes which form an energy transfer pair. Fluorescence intensity increases as the probe is cleaved. Published PCT application WO 96/21144 discloses continuous fluorometric assays in which enzyme-mediated cleavage of nucleic acids results in increased fluorescence. Fluorescence energy transfer is suggested for use in the methods, but only in the context of a method employing a single fluorescent label which is quenched by hybridization to the target.

Energy transfer and other fluorescence quenching detection methods have also been applied to detecting a target sequence by hybridization of a specific probe. Japanese Patent No. 93015439 B discloses methods for measuring polynucleotides by hybridizing the single-stranded target to a single-stranded polynucleotide probe tagged with two labels which form an energy transfer pair. The double-stranded hybrid is cleaved between the labels by a restriction enzyme and fluorescence of one of the labels is measured. A shortcoming of this method is that the restriction site in the probe must also be present in the target sequence being detected. S. S. Ghosh, et al. 1994. *Nucl. Acids Res.* 22, 3155–3159) describe restriction enzyme catalyzed cleavage of fluorophore-labeled oligonucleotides which are analyzed using fluorescence resonance energy transfer. In these assays, the complementary oligonucleotides are hybridized to produce the double-stranded restriction site, and one of the fluorescent labels is linked to each of the two strands. S. P. Lee, et al. (1994. *Anal. Biochem.* 220, 377–383) describe fluorescence "dequenching" techniques using restriction endonucleases to cleave double-stranded DNA. However, these methods relate to assays employing only a single fluorescent label which is quenched by interaction with the DNA, not by fluorescence energy transfer from a second fluorescent label. Hybridization of the labeled oligonucleotide to its complement and cleavage of the double-stranded restriction site reduced the non-transfer quenching of the label such that quenched fluorescence was totally recovered.

Signal primers (also referred to as detector probes) which hybridize to the target sequence downstream of the hybridization site of the amplification primers have been described for use in detection of nucleic acid amplification (U.S. Pat. No. 5,547,861). The signal primer is extended by the polymerase in a manner similar to extension of the amplification primers. Extension of the amplification primer displaces the extension product of the signal primer in a target amplification-dependent manner, producing a double-stranded secondary amplification product which may be detected as an indication of target amplification. The secondary amplification products generated from signal primers may be detected by means of a variety of labels and reporter groups, restriction sites in the signal primer which are cleaved to produce fragments of a characteristic size, capture groups, and structural features such as triple helices and recognition sites for double-stranded DNA binding proteins. Examples of detection methods for use with signal primers are described in U.S. Pat. No. 5,550,025 (incorporation of lipophilic dyes and restriction sites) and U.S. Pat. No. 5,593,867 (fluorescence polarization detection).

SUMMARY OF THE INVENTION

The present invention employs a detector nucleic acid for detection of nucleic acid target sequences by fluorescence quenching mechanisms. The detector nucleic acid comprises at least two oligonucleotides and is partially single-stranded and partially double-stranded. A first oligonucleotide is hybridized to at least one complementary second oligonucleotide which is shorter than the first oligonucleotide such that either the 5' or the 3' end of the first oligonucleotide forms a single-stranded tail region (referred to as the target binding sequence) which hybridizes to the target sequence. The first oligonucleotide and the shorter, complementary second oligonucleotide hybridize to form the intermolecularly base-paired, partially double-stranded detector nucleic acid under the selected reaction conditions for primer extension or hybridization to the target. The first oligonucleotide may be hybridized to a single second oligonucleotide such that the detector nucleic acid consists of two oligonucleotides. Alternatively, the longer first oligonucleotide may be hybridized to multiple shorter second oligonucleotides (typically 2–5 second oligonucleotides). The multiple second oligonucleotides hybridize to the first oligonucleotide and to each other such that a 3-way, 4-way, 5-way or 6-way oligonucleotide junction structure is formed in the double-stranded portion of the detector nucleic acid.

The detector nucleic acid is further modified by linkage to at least two dyes which form a donor/acceptor dye pair. Multiple donor/acceptor pairs may be linked to a detector nucleic acid consisting of two oligonucleotides, but are particularly advantageous in detector nucleic acids comprising greater than two oligonucleotides. One of the two dyes of a donor/acceptor pair is linked to the longer first oligonucleotide and the other is linked to a second oligonucleotide such that the dyes are in close spatial proximity when the first and second oligonucleotides are base-paired, resulting in quenching of donor dye fluorescence. If multiple second oligonucleotides are present in the detector nucleic acid, additional donor/acceptor pairs may be linked to opposite strands of paired second oligonucleotides such that quenching occurs. The detector nucleic acid remains in partially single-stranded, partially double-stranded, quenched conformation in the absence of target. In the presence of target, however, a second oligonucleotide of the detector nucleic acid is completely or partially displaced from the first oligonucleotide, increasing the distance between the donor and acceptor dyes and causing a change in fluorescence.

In alternative exemplary embodiments, the invention employs the detector nucleic acid as a signal primer in target amplification reactions for detecting target sequence amplification, in non-amplification based primer extension methods for detection of target sequences and in hybridization reactions for detection of target sequences.

The present invention provides an alternative to previously known restriction-based methods for separating donor and acceptor dyes onto independent fragments in the presence of a target. In the present invention there is no need to engineer a restriction site into the probe or primer and the restriction enzyme may be eliminated from the target detection reaction, reducing the cost of the assay.

DESCRIPTION OF THE DRAWINGS

FIG. 3 illustrates the reaction scheme wherein a detector nucleic acid comprising an oligonucleotide junction structure, exemplified as a 3-way junction, is employed as a signal primer according to the invention.

FIG. 4 shows the change in fluorescence intensity occurring in real-time as a target is amplified using the detector nucleic acids of the invention as signal primers.

DETAILED DESCRIPTION OF THE INVENTION

Figure 1:
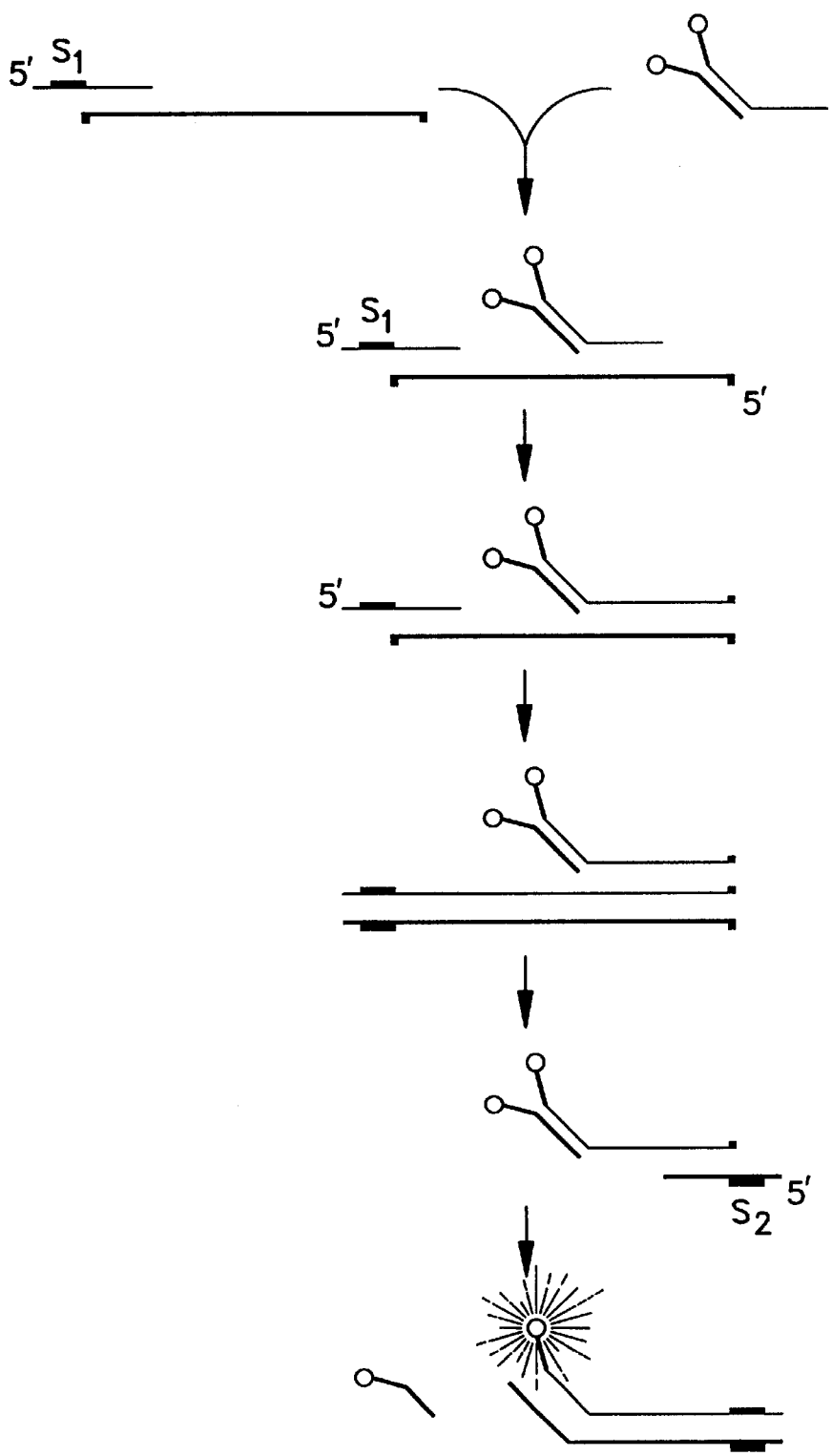
FIG. 1 illustrates the reaction scheme wherein a detector nucleic acid consisting of two oligonucleotides is employed as a signal primer according to the invention.

The present invention employs detector nucleic acids to produce reduced fluorescence quenching in a target-dependent manner. The detector nucleic acids contain a donor/acceptor dye pair linked such that fluorescence quenching occurs in the absence of target. In the presence of the target, complete or partial displacement of a second oligonucleotide intermolecularly base-paired with a first oligonucleotide in the detector nucleic acid increases the distance between the dyes, reducing fluorescence quenching. Displacement of the second oligonucleotide requires hybridization between the first oligonucleotide and the target. Reduced quenching is associated with a change in a fluorescence parameter (e.g., an increase in donor fluorescence intensity, a decrease in acceptor fluorescence intensity or a ratio of fluorescence before and after unfolding) which is monitored as a indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

Certain terms used herein are defined as follows:

An amplification primer is a primer for amplification of a target sequence by primer extension. For SDA, the 3' end of the amplification primer (the target binding sequence) hybridizes at the 3' end of the target sequence. The amplification primer comprises a recognition site for a restriction endonuclease near its 5' end. The recognition site is for a restriction endonuclease which will cleave one strand of a DNA duplex when the recognition site is he rimodified ("nicking"), as described in U.S. Pat Nos. 5,455,166; 5,270, 184 and; EP 0 684 315. A hemimodified recognition site is a double stranded recognition site for a restriction endonuclease in which one strand contains at least one derivatized nucleotide which causes the restriction endonuclease to nick the primer strand rather than cleave both strands of the recognition site. Usually, the primer strand of the hemimodified recognition site does not contain derivatized nucleotides and is nicked by the restriction endonuclease. Alternatively, the primer may contain derivatized nucleotides which cause the unmodified target strand to be protected from cleavage while the modified primer strand is nicked. Such restriction endonucleases can be identified in routine screening systems in which a derivatized dNTP is incorporated into a restriction endonuclease recognition site for the enzyme. Preferred hemimodified recognition sites are hemiphosphorothioated recognition sites for the restriction endonucleases HincII, BsoBI and BsrI. The amplification primer also comprises a 3'-OH group which is extendible by DNA polymerase when the target binding sequence of the amplification primer is hybridized to the target sequence. For the majority of the SDA reaction, the amplification primer is responsible for exponential amplification of the target sequence.

As no special sequences or structures are required to drive the amplification reaction, amplification primers for PCR may consist only of target binding sequences. Amplification primers for 3SR and NASBA, in contrast comprise an RNA polymerase promoter near the 5' end. The promoter is appended to the target sequence and serves to drive the amplification reaction by directing transcription of multiple RNA copies of the target.

Extension products are nucleic acids which comprise a primer or a portion of a primer and a newly synthesized strand which is the complement of the target sequence downstream of the primer binding site. Extension products result from hybridization of a primer to a target sequence and extension of the primer by polymerase using the target sequence as a template.

The terms target or target sequence refer to nucleic acid sequences to be amplified or detected. These include the original nucleic acid sequence to be amplified, its complementary second strand and either strand of a copy of the original sequence which is produced by replication or amplification. The target sequence may also be referred to as a template for extension of hybridized primers.

A detector nucleic acid comprises at least two oligonucleotides, a first of which is longer than the others. The oligonucleotides are hybridized in the detector nucleic acid such that the longer one forms a single-stranded 5' or 3' "tail" which hybridizes to the target sequence (the target binding sequence). At least one shorter, second oligonucleotide base-pairs with the longer oligonucleotide (i.e., it hybridizes) adjacent to the target binding sequence. Additional shorter, second oligonucleotides may also base-pair with each other and/or the longer first oligonucleotide to form oligonucleotide junction structures as is known in the art. The detector nucleic acids of the invention further comprise at least one donor/acceptor dye pair. The dyes are linked to the oligonucleotides of the detector nucleic acid such that donor fluorescence is quenched when they are intermolecularly base-paired, and displacement of a second oligonucleotide from the first results in a decrease in fluorescence quenching.

The detector nucleic acids of the invention comprise two or more oligonucleotides (typically about two to six oligonucleotides) which form a partially double-stranded and partially single-stranded nucleic acid molecule under the selected reaction conditions for primer extension or hybridization. In a preferred embodiment, a single shorter second oligonucleotide is intermolecularly base-paired to the longer first oligonucleotide at a position adjacent to the target binding sequence of the first oligonucleotide so that at least a portion of the target binding sequence forms a single-stranded 3' or 5' tail. This type of detector nucleic acid consists of two oligonucleotides. Alternatively, multiple shorter second oligonucleotides are intermolecularly base-paired to the longer first oligonucleotide and to each other to form a substantially double-stranded oligonucleotide junction structure adjacent to the target binding sequence. Oligonucleotide junctions are known in the art and are described, for example, by D. M. J. Lilley and R. M. Clegg (1993. *Annu. Rev. Biophys. Biomol. Struct.* 22, 299–328), M. Yang and D. P. Millar (1996. *Biochem.* 35, 7959–7967), J. E. Ladbury, et al. (1994). *Biochem.* 33, 6828–6833), J. Wang, et al. (1991. *Biochem.* 30, 5667'5674) and J. L. Kadrmas, et al. (1995. *Nucl. Acids Res.* 23, 2212'2222). In the detector nucleic acids of the invention, the portion of the first oligonucleotide not involved in the junction structure forms a single-stranded 3' or 5' tail. These detector nucleic acids typically consist of three to six oligonucleotides, but more complex junction structures comprising a greater number of oligonucleotides are possible for use in the invention. As used herein, the term "adjacent to the target binding sequence" means that all or part of the target binding sequence is left single-stranded in a 5' or 3' tail which is available for hybridization to the target. That is, the double-stranded portion of the detector nucleic acid does not comprise the entire target binding sequence. A portion of the target binding sequence may be involved in the intermolecular base-pairing of the adjacent double-stranded portion or the entire target binding sequence may form a single-stranded 5' or 3' tail in the detector nucleic acid. The remainder of the double-stranded portion of the detector nucleic acid is not complementary to the target. Mismatches in the intermolecularly base-paired portion of the detector nucleic acid may reduce the magnitude of the change in fluorescence in the presence of target but are acceptable if assay sensitivity is not a concern. Mismatches in the target binding sequence of the single-stranded tail are also acceptable but may similarly reduce assay sensitivity and/or specificity. However, it is a feature of the present invention that perfect base-pairing in both the double-stranded portion and the target binding sequence do not compromise the reaction. However, perfect matches in the sequences involved in hybridization improve assay specificity without significant negative effects on reaction kinetics.

The detector nucleic acid further comprises a donor dye which is a fluorophore and an acceptor for the donor fluorophore. In the two-oligonucleotide detector nucleic acid, one of the two dyes of the donor/acceptor pair is linked to each oligonucleotide comprising the detector nucleic acid such that the intermolecular base-pairing between the two oligonucleotides brings the dyes into close spatial proximity and results in fluorescence quenching. If there are two or more second oligonucleotides in the detector nucleic acid, forming an oligonucleotide junction, multiple donor/acceptor pairs may be linked to the first and second oligonucleotides such that the fluorescence of each donor is quenched by its corresponding acceptor in the junction structure and quenching is reduced when the junction is disrupted. That is, the two members of each donor/acceptor pair are preferably linked to different oligonucleotides in the detector nucleic acid. See, for example, FIG. 3. DNA junctions have been labeled and analyzed using fluorescence resonance energy transfer in the prior art, but these studies were for the purpose of analyzing the stereochemical conformation of the junction, not for detecting a selected target and the junctions therefore did not include target binding sequences in single-stranded tails (e.g., P. S. Eis and D. P. Millar. 1993. *Biochem.* 32, 13852–13860; M. Yang and D. P. Millar. 1996. *Biochem.* 35, 7959–7967; R. M. Clegg, et al. 1994. *Biophys. J.* 66, 99–109; R. M. Clegg, et al. 1993. *Br. J. Med. Res.* 26, 405–416; R. M. Clegg, et al. 1992. *Biochem.* 31, 4846–4856).

Preferably neither dye of the donor/acceptor pair is at the 3' terminus of the single-stranded tail of the detector nucleic acid when the detector nucleic acid is used as a primer, as a 3' terminal label may interfere with hybridization and/or extension of the oligonucleotide. However, a selected donor fluorophore and its corresponding acceptor may be linked at any position on their respective oligonucleotides which does not inhibit hybridization and/or extension, which results in donor quenching in the partially double-stranded detector nucleic acid molecule and which provides a change in a fluorescence parameter upon complete or partial displacement of the shorter oligonucleotide.

The donor and acceptor are linked to their respective oligonucleotides in the detector nucleic acid such that donor fluorescence is totally or partially quenched when the first and second oligonucleotides or the complementary portions of second oligonucleotides are intermolecularly base-paired. Quenching occurs when the two dyes are in sufficiently close proximity in the partially double-stranded detector nucleic acid. Target-dependent disruption of the duplex with separation of the base-paired oligonucleotides, each linked to one of the two dyes, increases the distance between the members of the donor/acceptor pair and produces a detectable change in a fluorescence parameter of either the donor or the acceptor due to reduced quenching. Both members of the pair may be linked to sequences involved in formation of the intermolecular hydrogen bonds in the double-stranded portion of the detector nucleic acid. Alternatively, one member of the pair may be linked within the base-paired sequence of a second, shorter oligonucleotide and the other may be linked to the single-stranded target binding sequence of the longer first oligonucleotide hybridized to it. Preferably, both dyes are linked so that they are both incorporated into intermolecularly base-paired sequences of the detector nucleic acid (i.e., one dye in or near each of two complementary sequences which are involved in intermolecular base-pairing).

In general, the overall length of the sequences involved in intermolecular base-pairing between the first oligonucleotide and a second oligonucleotide in the detector nucleic acid is not critical. The appropriate length is determined by the number of nucleotides required for stable base-pairing to maintain a partially double-stranded molecule under the selected reaction conditions. For convenience, the sequences involved in first oligonucleotide/second oligonucleotide base-pairing are typically between about 8 and 75 nucleotides in length. The maximum length is limited only by practical concerns such as the ease and efficiency of oligonucleotide synthesis and recovery. The length of sequences involved in intermolecular base-pairing between second oligonucleotides in a junction structure is selected such that the $T_m$ is low enough to cause the second oligonucleotides to dissociate from each other into single strands under the conditions of the reaction when the oligonucleotide junction structure is displaced from the first oligonucleotide. The sequences involved in intra-second oligonucleotide base-pairing are therefore typically relatively short (e.g., about 2–10 nucleotides).

The sequence of the double-stranded portion of the detector nucleic acid is also selected such that at least a portion of it is not complementary to the target and such that it is relatively stable at the temperature of the reaction which serves to disrupt it. However, it must not be so stable that hybridization to the target is unacceptably slow or so stable that the polymerase is unable to displace the second oligonucleotide from the first oligonucleotide for synthesis of the complementary strand. Preferably, the $T_m$ of the double-stranded portion of the detector nucleic acid involving hybridization between the first oligonucleotide and a second oligonucleotide is equal to or greater than the temperature at which the displacement reaction will occur, but it may be lower. If the $T_m$ of this segment is less than the reaction temperature, more than half of the detector nucleic acid molecules will be fully single-stranded independent of the presence of the target. This reduces assay sensitivity but may be acceptable when relatively high quantities of target are present. Typically, the $T_m$ of the double-stranded portion of the detector nucleic acid involving hybridization between the first oligonucleotide and a second oligonucleotide is selected to be equal to or up to about 30° C. higher than the temperature of the reaction which displaces the second oligonucleotide. Most preferably, the $T_m$ is about 10–20° C. higher than the reaction which displaces the second oligonucleotide.

In the oligonucleotide junction, sequences involved in base-pairing between second oligonucleotides are selected such that there is stable hybridization between second oligonucleotides under the selected reaction conditions when the junction structure is hybridized to the first oligonucleotide and the hybrids are destabilized and at least partially dissociated under the selected reaction conditions when the oligonucleotide junction is not hybridized to the first oligonucleotide. The $T_m$ of the inter-second oligonucleotide hybrids may be used as is known in the art to adjust the sequences of the second oligonucleotides to obtain this result, and it is generally selected to be approximately equal to or less than the reaction temperature. The length and nucleotide composition of the sequences involved in base-pairing is one factor affecting the $T_m$, with shorter sequences and relatively AT-rich sequences generally contributing to a lower $T_m$. The presence of polymerase in certain assays may increase the stability of the double-stranded portions of the molecule, partially compensating for the effects of increased temperature.

Because the second oligonucleotide is shorter than the first oligonucleotide to which it hybridizes, the portion of the first oligonucleotide which is not intermolecularly base-paired with the second oligonucleotide forms a 5' or 3' single-stranded tail. The single-stranded tail portion of the detector nucleic acid is complementary to the target sequence to be detected and serves to hybridize the detector nucleic acid to the target sequence. Features other than complementarity to the target sequence are generally not critical, except that the sequence of the tail is preferably selected such that it will form a stable duplex with the target under the selected reaction conditions and provide the desired degree of detection specificity as is known in the art. To favor hybridization to target, the sequence of the single-stranded target binding tail region of the first oligonucleotide is also preferably selected such that the $T_m$ of the target binding sequence/target duplex is equal to or higher than the reaction temperature. Although the sequence of the target binding region is dictated by the sequence of the target to be detected, adjustments in the $T_m$ of the target binding sequence of the detector nucleic acid may be made, for example, by adjusting its length.

In a first embodiment, the detector nucleic acids of the invention may be used as signal primers in amplification reactions to generate secondary amplification products with an accompanying change in a fluorescence parameter. When used as a signal primer in nucleic acid amplification reactions the single-stranded tail of the detector nucleic acid comprises the 3' end of the first oligonucleotide to allow for primer extension. The double-stranded portion of the detector nucleic acid is therefore 5' to the target binding sequence when the detector nucleic acid is used as a signal primer. The term "5' to the target binding sequence" indicates that all or part of the target binding sequence is present as a single-stranded 3' tail. That is, the segment of the first oligonucleotide involved in intermolecular base-pairing with a second oligonucleotide may comprise a portion of the target binding sequence or the entire target binding sequence may be present in the single-stranded 3' tail. The two-oligonucleotide detector nucleic acid signal primer reaction is illustrated in FIG. 1 by way of example, and may be summarized as follows. Via the single-stranded tail of the first oligonucleotide, the detector nucleic acid signal primer hybridizes to one strand of the target sequence downstream of an amplification primer. Both the amplification primer and the first oligonucleotide are extended by DNA polymerase using the target sequence as a template. The first oligonucleotide extension product, with the second oligonucleotide still hybridized to it, is displaced from the template by extension of the upstream amplification primer. The detector nucleic acid is still partially double-stranded after displacement of the first oligonucleotide extension product from the target. The extended, displaced detector nucleic acid in turn serves as a template for hybridization and extension of a second amplification primer, rendering the single-stranded portion of the detector nucleic acid extension product double-stranded. Polymerization of a new strand complementary to the first oligonucleotide also displaces the second oligonucleotide due to the strand displacing activity of the polymerase and separates the member of the donor/acceptor pair linked to the first oligonucleotide from the member of the donor/acceptor linked to the second oligonucleotide. If multiple second oligonucleotides are hybridized to each other in an oligonucleotide junction structure in the detector nucleic acid signal primer (illustrated in FIG. 3 by way of example), synthesis of the strand complementary to the first oligonucleotide displaces the junction structure from the first oligonucleotide. The regions of base-pairing between second oligonucleotides in the oligonucleotide junction are sufficiently short that they dissociate into single strands when separated from the first oligonucleotide, separating the members of each donor/acceptor pair onto separate single strands.

A second detector nucleic acid which hybridizes to the second, complementary strand of a double-stranded target sequence may optionally be included in the reaction (not shown in FIGS. 1 and 3). The second detector nucleic acid hybridizes to the second strand of the target sequence downstream of the second amplification primer and is extended and displaced by extension of the second amplification primer. The single-stranded portion of the second detector nucleic acid extension product is rendered double-stranded with displacement of the second oligonucleotide or junction by hybridization and extension of the first amplification primer. Multiple detector nucleic acids per strand of target may be employed if desired, each hybridizing to the target sequence downstream of the other on the same strand, and all detector nucleic acids being hybridized downstream of the amplification primer. In this manner, each detector nucleic acid is displaced by extension of the upstream detector nucleic acid and the most 5' detector nucleic acid is displaced by the amplification primer. Use of multiple detector nucleic acids has the advantage of increasing or amplifying the signal generated per target, with an increase in sensitivity of the assay.

As shown in FIGS. 1 and 3, the single-stranded portion of the detector nucleic acid is converted to double-stranded form by hybridization and extension of an amplification primer. Strand displacement by the polymerase also displaces the second oligonucleotide(s) from the first oligonucleotide as the polymerase synthesizes the complement of the first oligonucleotide. As the strand displacing activity of the polymerase separates a second oligonucleotide linked to one member of a donor/acceptor pair from the first oligonucleotide linked to the corresponding member of the pair, the distance between the donor and acceptor dye is increased, thereby reducing quenching of donor fluorescence. That is, the single-stranded, displaced second oligonucleotide and the double-stranded first oligonucleotide thus produced, each linked to one of the two dyes, are free to independently diffuse in the reaction solution. The reduction in quenching is enhanced when additional donor/acceptor pairs are linked to additional second oligonucleotides hybridized to the first oligonucleotide and/or to each other. As the displaced oligonucleotide junction structure dissociates into single strands, the reduction in quenching of each donor fluorophore contributes to the total increase in fluorescence. The associated change in fluorescence of either the donor or acceptor dye may be monitored or detected as an indication of amplification of the target sequence. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair (e.g., fluorescence lifetime) may also be monitored. A change in fluorescence intensity of the donor or acceptor may also be detected as a change in a ratio of donor and/or acceptor fluorescence intensities. For example, a change in fluorescence intensity may be detected as a) an increase in the ratio of donor fluorophore fluorescence after displacement of the second oligonucleotide and donor fluorophore fluorescence in the detector nucleic acid prior to displacement of the second oligonucleotide, or b) when the acceptor is a fluorophore, as a decrease in the ratio of acceptor fluorescence after displacement of the second oligonucleotide and acceptor fluorescence in the detector nucleic acid prior to displacement of the second oligonucleotide.

It will be apparent that, in addition to SDA, the detector nucleic acids of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'→3' exonuclease activity (e.g., Sequencing Grade Taq from Promega or exo⁻ Vent or exo⁻ Deep Vent from New England BioLabs) in the PCR. The detector nucleic acid signal primers hybridize to the target downstream from the PCR amplification primers. They are extended, displaced from the target and rendered double-stranded with displacement of the second oligonucleotide or oligonucleotide junction essentially as described for SDA. As in SDA systems, displacement of the second oligonucleotide and separation of donor/acceptor dye pairs reduces fluorescence quenching, with a change in a fluorescence parameter, such as intensity, serving as an indication of target amplification.

For adaptation of the inventive methods to 3SR, TMA or NASBA, a 5'→3' exonuclease deficient reverse transcriptase with strand displacing activity is employed, with hybridization of the detector nucleic acid to the RNA target downstream of an amplification primer which contains an RNA polymerase promoter. In a reaction scheme similar to that previously described, the hybridized detector nucleic acid comprising the hybridized second oligonucleotide is 1) extended, and 2) displaced by extension of the upstream amplification primer. The displaced extension product is then made entirely double-stranded by hybridization and extension of the second amplification primer. This displaces the second oligonucleotide or oligonucleotide junction from the first oligonucleotide of the detector nucleic acid, increasing the distance between the donor and acceptor dyes and reducing fluorescence quenching of the donor fluorophore. The detector nucleic acid signal primer for 3SR or NASBA does not contain an RNA polymerase promoter sequence and therefore cannot function as an amplification primer, reducing nonspecific background signal. This is analogous to the signal primer in SDA, which does not contain a nickable RERS and therefore does not significantly contribute to exponential background amplification of non-specific targets.

For reduced background, it is preferred that detector nucleic acids be used as signal primers in the methods of the invention, with the detector nucleic acid extension product being separated from the target sequence by displacement due to extension of the upstream amplification primer. However, it will be apparent that the amplification primers known for use in the various nucleic acid amplification reactions may also be modified by addition of a 5' intermolecularly base-paired sequence as described for detector nucleic acid signal primers. In this embodiment, the amplification primer extension product, with the 5' double-stranded portion, may be separated from the target sequence by displacement due to extension of an upstream non-amplification primer (e.g., bumper primers as in SDA), by denaturation (e.g., heating as in PCR) or by enzymatic digestion of the target strand (e.g., RNase H as in 3SR). Amplification primers comprising the 5' double-stranded portion and the donor/acceptor dye pair eliminate the need for the additional detector nucleic acid in the reaction, but because background may be higher in this embodiment the sensitivity of the assay may be decreased. For PCR, the amplification primer is modified by addition of sequences 5' to the target binding sequence which are complementary to the second oligonucleotide. The second oligonucleotide is then hybridized to the added 5' sequence. This primer is structurally identical to the PCR detector nucleic acid signal primer described above. Functionally, however, it is different in that there is no downstream primer to be extended and displaced and the amplification primer itself provides the change in fluorescence. For 3SR, NASBA and TMA, the sequence complementary to the second oligonucleotide may be placed 5' to the promoter of an amplification primer and the second oligonucleotide hybridized to it so that the second oligonucleotide or oligonucleotide junction is displaced and the first oligonucleotide is rendered totally double-stranded in the double-stranded DNA portion of the amplification cycle. A second amplification primer which does not contain a promoter sequence (e.g., as in NASBA) may also or alternatively contain the sequences complementary to the hybridized second oligonucleotide 5' to the target binding sequence.

In alternative embodiments, the detector nucleic acid may be used in non-amplification based assay formats to detect target oligonucleotides. In a first non-amplification embodiment, the 3' single-stranded target binding sequence of the first oligonucleotide of the detector nucleic acid hybridizes to the 3' end of the target oligonucleotide such that the base-paired duplex portion of the detector nucleic acid forms a 5' overhang. The target sequence functions as a primer in a primer extension reaction to synthesize a strand complementary to the first oligonucleotide using a strand displacing polymerase which extends the target sequence using the 5' overhang (i.e., the sequence of the first oligonucleotide which is base-paired to the second oligonucleotide) as a template. If the target binding sequence of the detector nucleic acid hybridizes to only a portion of the target sequence, the target sequence also forms a 5' overhang and the first oligonucleotide of the detector nucleic acid is similarly extended using the 5' overhang of the target as a template. If the target binding sequence of the detector nucleic acid is complementary to the entire length of the target sequence only the target is extended. In either case, the second oligonucleotide(s) of the detector nucleic acid is/are thus displaced from the first oligonucleotide with an accompanying change in fluorescence parameter. Extension and displacement of the second oligonucleotide(s) to produce a change in fluorescence can take place only in the presence of target.

In a second non-amplification based embodiment of the invention, the first oligonucleotide of the detector nucleic acid is hybridized to the target sequence such that a change in fluorescence occurs upon hybridization. The single-stranded target binding sequence may therefore be at either the 5' or 3' end of the first oligonucleotide when the detector nucleic acid is used as a hybridization probe. That is, because primer extension is not necessary, the double-stranded portion of the detector nucleic acid may be either 5' or 3' to the single-stranded tail, optionally comprising a portion of the target binding sequence. In this embodiment, the intermolecularly base-paired portion of the detector nucleic acid preferably comprises a portion of the target binding sequence with the remaining target binding sequence present in the 3' or 5' single-stranded tail which is available for non-competitive hybridization to the target. Hybridization thereby partially or completely disrupts the duplex portion of the detector nucleic acid, resulting in partial or total displacement of the second oligonucleotide, increased distance between the two dyes and reduced fluorescence quenching. However, changes in fluorescence may also be observed upon hybridization when the target binding sequence is entirely in the single-stranded tail of the detector nucleic acid and no base-pairing between target and the sequence of the first oligonucleotide involved in base-pairing with the second oligonucleotide is possible.

When target is present, the detector nucleic acid hybridization probe initially hybridizes to it noncompetitively by means of the single-stranded tail. This brings any target-complementary sequences of the first oligonucleotide which may be present in the duplex portion of the detector nucleic acid into close proximity with their complementary sequences in the target. The target binding sequence of the first oligonucleotide in the duplex portion hybridizes to its complementary sequence in the target, thus disrupting the intermolecular base-pairing in the detector nucleic acid and increasing the distance between the donor and acceptor dyes as the second oligonucleotide is partially or completely displaced from the first oligonucleotide by competitive hybridization. The resulting change in a fluorescence parameter may be detected as an indication of the presence of the target sequence. Binding of the single-stranded 5' or 3' tail of the first oligonucleotide to the target sequence is believed to facilitate disruption of the detector nucleic acid duplex by holding the complementary sequences of the target and the base-paired portion of the first oligonucleotide in close proximity, better favoring intermolecular base-pairing between first oligonucleotide and target. Such cooperative binding may allow the target to more effectively compete against the corresponding sequence in the second oligonucleotide for hybridization to the first oligonucleotide. Without cooperative binding provided by the single-stranded target binding sequence in the 3' or 5' tail of the first oligonucleotide, the duplex portion of the detector nucleic acid would tend to remain intact and little or no change in fluorescence is likely to be observed even in the presence of target.

It is therefore a feature of the invention that the target is not initially required to hybridize to the base-paired sequences in the detector nucleic acid. Initial competitive hybridization reduces the affinity of a probe or primer for the target and decreases assay sensitivity. In contrast, the initial non-competitive binding of the invention better favors intermolecular hybridization in any subsequent competitive hybridization reaction. The length of the single-stranded 3' or 5' tail may be adjusted without affecting the thermodynamic properties of the duplex portion of the detector nucleic acid, so target hybridization may be optimized without requiring redesign of the duplex portion of the detector nucleic acid. This greatly simplifies probe and primer design as compared to the prior art.

In addition to detecting the presence or absence of target and detecting amplification of target, the inventive detector nucleic acids may be used as primers or hybridization probes to distinguish between targets which differ by one or more nucleotides. To perform such analyses, the target binding sequence in the single-stranded tail of the detector nucleic acid is selected such that stable hybridization to the target occurs only when hybridization is enhanced by base-pairing of the target with one or more nucleotides of the first oligonucleotide involved in intermolecular base-pairing in the duplex portion of the detector nucleic acid. The detector nucleic acid is further designed such that hybridization to a target containing one or more nucleotide differences to be detected would result in one or more mismatched base pairs in either the tail sequence or in the sequence of the first oligonucleotide which hybridizes to the second oligonucleotide. The reduced stability of the mismatch in conjunction with competition from rehybridization of the first and second oligonucleotides reduces hybridization to the target containing the nucleotide difference(s), thus reducing the magnitude of the change in fluorescence as compared to a perfectly matched target (i.e., a target without the nucleotide difference). Increasing numbers of mismatches produce correspondingly smaller changes in fluorescence. Fewer mismatches result in correspondingly larger changes in fluorescence. As the number of mismatches decreases, the magnitude of the fluorescence change approaches that observed for perfectly matched sequences, with the ability to discriminate single nucleotide differences. Similar methods may be used to detect frame shift mutations.

The change in fluorescence resulting from complete or partial displacement of the second oligonucleotide may be detected at a selected endpoint in the reaction. However, because completely or partially displaced second oligonucleotides are produced concurrently with hybridization or primer extension, the change in fluorescence may also be monitored as the reaction is occurring, i.e., in "real-time". This homogeneous, real-time assay format can be used to provide semi-quantitative or quantitative information about the initial amount of target present. For example, the rate at which fluorescence intensity changes during the second oligonucleotide displacement reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the second oligonucleotide displacement reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector nucleic acid functions as a primer are typically performed in solution. Hybridization assays using the detector nucleic acids of the invention may also be performed in solution (e.g., as homogeneous real-time assays) but are also particularly well-suited to solid phase assays for real-time or endpoint detection of target. In a solid phase assay, detector nucleic acids may be immobilized on the solid phase (e.g., beads, membranes or the reaction vessel) via internal or terminal labels using methods known in the art. For example, a biotin-labeled detector nucleic acid may be immobilized on an avidin-modified solid phase where it will produce a change in fluorescence when exposed to the target under appropriate hybridization conditions. Capture of the target in this manner facilitates separation of the target from the sample and allows removal of substances in the sample which may interfere with detection of the signal or other aspects of the assay.

Many donor/acceptor dye pairs known in the art are useful in the present invention. These include, for example, fluorescein isothiocyanate (FITC)/tetramethylrhodamine isothiocyanate (TRITC), FITC/Texas Red™ (Molecular Probes), FITC/N-hydroxysuccinimidyl 1-pyrenebutyrate (PYB), FITC/eosin isothiocyanate (EITC), N-hydroxysuccinimidyl 1-pyrenesulfonate (PYS)/FITC, FITC/Rhodamine X, FITC/tetramethylrhodamine (TAMRA), and others. The selection of a particular donor/acceptor fluorophore pair is not critical. For energy transfer quenching mechanisms it is only necessary that the emission wavelengths of the donor fluorophore overlap the excitation wavelengths of the acceptor, i.e., there must be sufficient spectral overlap between the two dyes to allow efficient energy transfer, charge transfer or fluorescence quenching. P-(dimethyl aminophenylazo)benzoic acid (DABCYL) is a non-fluorescent acceptor dye which effectively quenches fluorescence from an adjacent fluorophore, e.g., fluorescein or 5-(2'-aminoethyl)aminonaphthalene (EDANS). Certain donor/acceptor pairs are exemplified above and in the following Examples, however, others will be apparent to those skilled in the art and are also useful in the invention. Any dye pair which produces fluorescence quenching in the detector nucleic acids of the invention are suitable for use in the methods of the invention, regardless of the mechanism by which quenching occurs. Terminal and internal labeling methods are also known in the art and may be routinely used to link the donor and acceptor dyes at their respective sites in the detector nucleic acid.

Target DNA for the following experimental examples was prepared from stocks of *Chlamydia trachomatis* elementary bodies (EB's) stored at concentrations of $10^6$ EB's/$\mu$L in 50% glycerol. EB stock solutions were diluted 1:10 in water, boiled for 15 minutes and prepared as 10-fold serial dilutions in 10 ng/$\mu$L human placental DNA. The donor fluorophore was conjugated to the 5' phosphate. Measurements were obtained with an SLM 8100 research grade fluorometer equipped with a circulating bath for maintaining sample compartment temperature, a xenon arc lamp and grating monochromators for controlling excitation and emission wavelengths. Experiments with fluorescein (FAM) as the donor used 488 nm for the excitation wavelength and 525 nm for emission.

EXAMPLE 1

SDA was performed generally as described in EP 0 684 315, with addition of a detector nucleic acid signal primer labeled at the 5' end of the first oligonucleotide with FAM and at the 3' end of the second oligonucleotide with Dabcyl. The final concentrations of components in each 100 $\mu$L reaction were 40 mM $K_iPO_4$ pH 7.5, 6 mM MgOAc, 0.2 mM each dTTP, dGTP, dATP, 1.4 mM dCTP$\alpha$S, 20 $\mu$g/mL acetylated BSA, 3% DMSO, 8% (v/v) glycerol, 100 ng human placental DNA, 25 units Bst polymerase (exo⁻ klenow fragment, New England BioLabs), 150 units AvaI (New England BioLabs, Beverly, Mass.), and DNA from 0, 10, 100 or 1,000 *Chlamydia trachomatis* elementary bodies. Each sample further contained the following primers at the indicated concentrations:

Detector nucleic acid (First oligonucleotide, SEQ ID NO:1, 200 nM)
TAGCCGACGTGCGAGCCGA
<u>TAGAGTCTTCAAATATCAGAGCTTTACCTAACAA</u>
Detector nucleic acid (Second oligonucleotide, SEQ ID NO:2, 400 nM)
ACTCTATCGGCTCGCACGTCGGCTA
Amplification primer S1.1 (SEQ ID NO:3, 750 nM)
ACCGCATCGAATCGATGTCTCGGGTA-GAAAATCGCATGCAAGATA
Amplification primer S2.1 (SEQ ID NO:4, 188 nM)
CGATTCCGCTCCAGACTTCTCGGGAGCT-GCCTCAGAATATACTCAG
Bumper primer B1 (SEQ ID NO:5, 75 nM)
TAAACATGAAAACTCGTTCCG
Bumper primer B2 (SEQ ID NO:6, 75 nM)
TTTTATGATGAGAACACTTAAACTCA The detector nucleic acid contained a sequence (underlined) which was complementary to both the target and the second oligonucleotide. The 0 target sample also contained 5 mM EDTA to disable the SDA reaction. Each reaction was assembled to contain all reagents except Bst and AvaI, and the samples were then heated for 2 min. at 95° C. They were transferred to a 53.5° C. water bath for 3–5 min. and the enzymes were added for a total sample volume of 100 $\mu$L. The samples were then transferred to 225 $\mu$L cuvettes and placed into a research grade SLM 8100 spectrofluorometer (Spectronic Instruments, Rochester, N.Y.). The temperature of the cuvettes was maintained at 53–54° C. by a circulating water bath, and the fluorescence emission of each cuvette at 520 nm ($\lambda_{excitation}$=488 nm) was recorded every 8 sec. Reactions were typically followed for 60–90 min.

Figure 2:
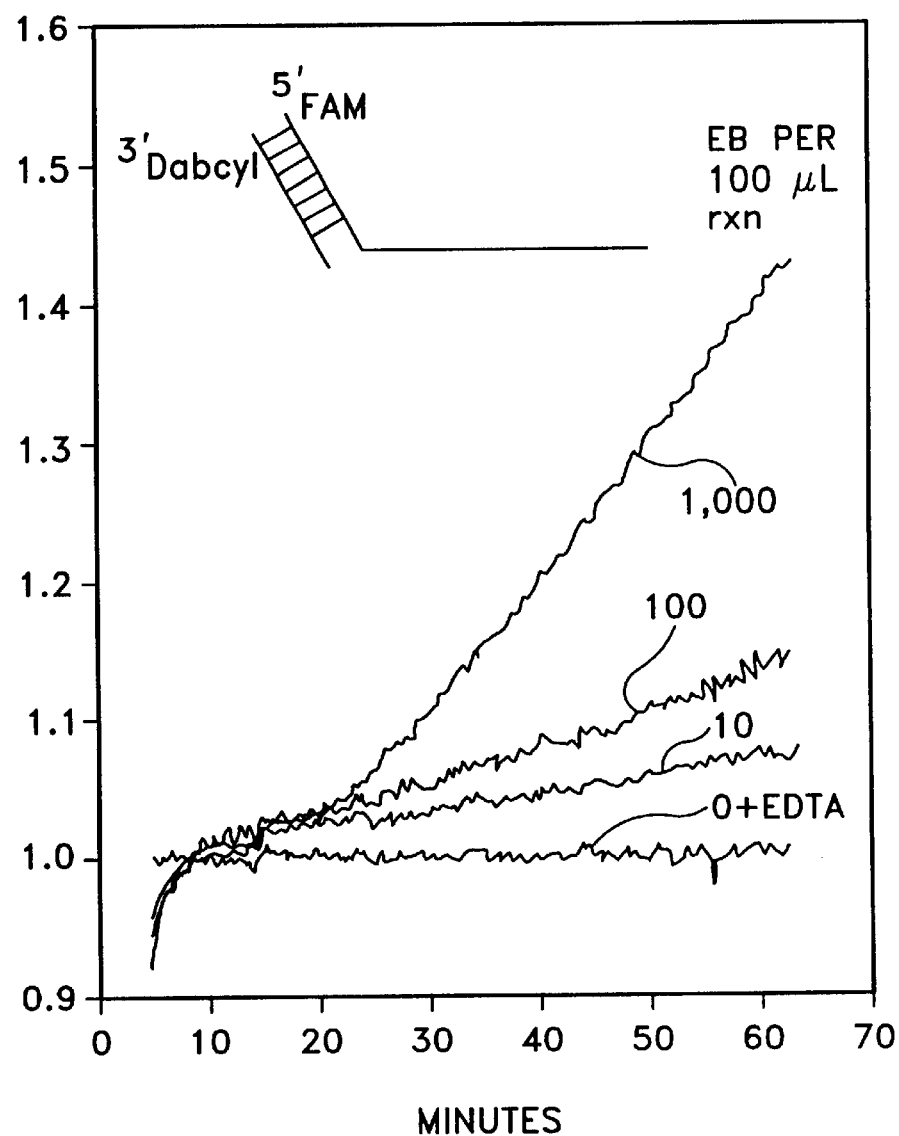
FIG. 2 shows the change in fluorescence intensity occurring in real-time as a target is amplified using the detector nucleic acids of the invention as signal primers.

The results are shown in FIG. 2. Fluorescence remained low (quenched) in the control reaction in which amplification was disabled, but increased measurably in reactions containing 10, 100 and 1,000 targets, demonstrating specific detection of target amplification. In addition, the rate of increase in fluorescence intensity of the donor (a measure of the rate of decrease in donor quenching) was more rapid in samples containing higher numbers of initial target. The rate of increase in donor fluorescence therefore provides not only detection of amplification in real-time, but also a semi-quantitative or relative measure of initial target levels. By comparing the rate of increase in fluorescence in a sample containing an unknown amount of target to the increase in fluorescence in a series of reactions containing varying known amounts of target (producing a standard curve as is known in the art) a quantitative measure of target levels in the unknown sample may be obtained. Alternatively, detection of an increase in fluorescence intensity above a predetermined threshold value may be used as an indication that the target is present and amplified in a simple positive/negative assay format.

EXAMPLE 2

The experiment of Example 1 was repeated, substituting a detector nucleic acid in which the target binding sequence of the first oligonucleotide did not extend into the double-stranded portion of the molecule (SEQ ID NO:7, labeled at the 5' end with fluorescein)
TAGACGTGCGAGCGGACTCAGTCT-TCAAATATCAGAGCTTTACCTAACAA
SEQ ID NO:8, labeled at the 3' end with either Dabcyl or ROX, was used as the second oligonucleotide in the detector nucleic acid and was present in the reaction in 3-fold excess over SEQ ID NO:7. In this experiment, the 0 control sample contained no target. The results are shown in FIG. 4. Fluorescence remained low (quenched) in the control reaction containing no target (no amplification) but increased measurably in reactions containing 100, 1,000 and 10,000 targets, demonstrating specific detection of target amplification. As before, the rate of increase in fluorescence intensity of the donor was more rapid in samples containing higher numbers of initial target, providing a semi-quantitative or relative measure of initial target levels as well as means for quantitative measurement of target levels in a unknown sample.

EXAMPLE 3

A detector nucleic acid comprising a 3-way oligonucleotide junction structure and two donor/acceptor dye pairs was designed using the following oligonucleotides:

First Oligonucleotide (SEQ ID NO:8, labeled at the 5' end with fluorescein)

GGAGCGAGCGAAGTGTCCTGGCTA-GAGTCTTCAAATATCAGAGCTTTACCTAACAA

Second Oligonucleotide #1 (SEQ ID NO:9, labeled at the 3' end with fluorescein)

GCCAGGACACGGAGAGG

Second Oligonucleotide #2 (SEQ ID NO:10, labeled at the 5' and 3' ends with Dabcyl)

CCTCTCCCGCTCGCTCC

Two 100 µL cuvettes containing 50 mM TRIS-HCl, pH 8.0, 10 mM MgCl$_2$, 50 mM NaCl, 10 mM dTTP, 10 mM dCTP, 10 mM dGTP, 10 mM dATP, 5 units exo⁻ Klenow, and varying amounts of the 3-way junction detector nucleic acid (50 nM SEQ ID NO:8, 50 nM SEQ ID NO:9 and 100 nM SEQ ID NO:10) were prepared and placed in an SLM 8100 fluorometer with the sample chamber preheated to 37° C. The control reaction contained a detector nucleic acid consisting of the first oligonucleotide (50 nM SEQ ID NO:8) and a single second oligonucleotide (100 nM SEQ ID NO:10), resulting in a detector nucleic acid having a single dye pair. Initial emission scans were taken (excitation at 488 nm, slits at 1 nm/1 nm; emission at 520 nm, slits at 5 nm/5 nm). The fluorescence intensity was monitored as a function of time to verify the absence of photobleaching. After a few minutes, 500 nM of a primer complementary to the 3' end of SEQ ID NO:8 (JBP59, TTGTTAGGTAAAGCTCTGATATTTGAAG, SEQ ID NO:11) was added to each cuvette to begin polymerase extension. When the intensity of the fluorescent signal had plateaued, emission scans were repeated. The results are shown in the following Table:

TABLE

| | Fluorescence Intensity | | |
|---|---|---|---|
| | pre-extension | post-extension | signal change |
| 3-way junction (2 dye pairs) | 3200 | 6800 | 3600 |
| single second oligo (1 dye pair) | 1300 | 4000 | 2700 |

These results demonstrate a greater increase in fluorescence intensity in the presence of target for the 3-way junction detector nucleic acid as compared to the detector nucleic acid consisting of only a single second oligonucleotide and one dye pair. That is, the presence of the additional "arms" in the double-stranded portion of the detector nucleic acid, provided by the oligonucleotide junction structure, allow linkage of additional fluorescent donor/acceptor pairs, increasing the change in fluorescent signal in the presence of target.

---

What is claimed is:

1. A method for detecting a target nucleic acid sequence comprising:
   a) noncompetitively hybridizing a detector nucleic acid to the target nucleic acid sequence, the detector nucleic acid comprising a first oligonucleotide hybridized to a second oligonucleotide;
   b) separating the second oligonucleotide from the first oligonucleotide in a target dependent manner, and;
   c) detecting separation as an indication of the presence of the target nucleic acid sequence.

2. The method of claim 1 wherein the second oligonucleotide is separated in a primer extension reaction.

3. The method of claim 2 wherein the second oligonucleotide is separated by extension of the target nucleic acid sequence using the first oligonucleotide as a template.

4. The method of claim 2 wherein the second oligonucleotide is separated in a target amplification reaction.

5. The method of claim 1 wherein separation is detected by a change in a fluorescence parameter.

6. The method of claim 5 wherein the detector nucleic acid is labeled with a donor/quencher dye pair and separation results in a change in fluorescence quenching.

7. The method of claim 5 wherein separation is detected by a change in fluorescence intensity.

8. The method of claim 1 wherein the first oligonucleotide is hybridized to multiple second oligonucleotides to form an oligonucleotide junction structure.

9. A detector nucleic acid for detecting a target nucleic acid sequence comprising a first oligonucleotide hybridized to a second oligonucleotide such that the detector nucleic acid hybridizes non-competitively to the target nucleic acid and wherein the detector nucleic acid is labeled such that separation of the second oligonucleotide from the first oligonucleotide is detectable.

10. The detector nucleic acid of claim 9 wherein the second oligonucleotide is shorter than the first oligonucleotide.

11. The detector nucleic acid of claim 9 wherein the first oligonucleotide is hybridized to multiple second oligonucleotides to form an oligonucleotide junction structure.

12. The detector nucleic acid of claim 9 which comprises an intermolecularly base-paired portion and a single-stranded target binding sequence, wherein the intermolecularly base-paired portion comprises a portion of the target binding sequence and a portion which is not complementary to the target nucleic acid sequence.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
      (A) LENGTH: 53 base pairs
      (B) TYPE: nucleic acid
      (C) STRANDEDNESS: single
      (D) TOPOLOGY: linear (xi) SEQUENCE DESCRIPTION: SEQ ID NO:1:

TAGCCGACGT GCGAGCCGAT AGAGTCTTCA AATATCAGAG CTTTACCTAA CAA      53

(2) INFORMATION FOR SEQ ID NO:2:

(i) SEQUENCE CHARACTERISTICS:
      (A) LENGTH: 25 base pairs
      (B) TYPE: nucleic acid
      (C) STRANDEDNESS: single
      (D) TOPOLOGY: linear (xi) SEQUENCE DESCRIPTION: SEQ ID NO:2:

ACTCTATCGG CTCGCACGTC GGCTA      25

(2) INFORMATION FOR SEQ ID NO:3:

(i) SEQUENCE CHARACTERISTICS:
      (A) LENGTH: 45 base pairs (B) TYPE: nucleic acid
        (C) STRANDEDNESS: single
        (D) TOPOLOGY: linear (xi) SEQUENCE DESCRIPTION: SEQ ID NO:3:

ACCGCATCGA ATCGATGTCT CGGGTAGAAA ATCGCATGCA AGATA                45

(2) INFORMATION FOR SEQ ID NO:4:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (xi) SEQUENCE DESCRIPTION: SEQ ID NO:4:

CGATTCCGCT CCAGACTTCT CGGGAGCTGC CTCAGAATAT ACTCAG              46

(2) INFORMATION FOR SEQ ID NO:5:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:5:

TAAACATGAA AACTCGTTCC G                                         21

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:6:

TTTTATGATG AGAACACTTA AACTCA                                    26

(2) INFORMATION FOR SEQ ID NO:7:

(i) SEQUENCE CHARACTERISTICS:
        (A) LENGTH: 50 base pairs
        (B) TYPE: nucleic acid
        (C) STRANDEDNESS: single
        (D) TOPOLOGY: linear (xi) SEQUENCE DESCRIPTION: SEQ ID NO:7:

TAGACGTGCG AGCGGACTCA GTCTTCAAAT ATCAGAGCTT TACCTAACAA          50

(2) INFORMATION FOR SEQ ID NO:8:

(i) SEQUENCE CHARACTERISTICS:
        (A) LENGTH: 56 base pairs
        (B) TYPE: nucleic acid
        (C) STRANDEDNESS: single
        (D) TOPOLOGY: linear (xi) SEQUENCE DESCRIPTION: SEQ ID NO:8:

GGAGCGAGCG AAGTGTCCTG GCTAGAGTCT TCAAATATCA GAGCTTTACC TAACAA   56

(2) INFORMATION FOR SEQ ID NO:9:

(i) SEQUENCE CHARACTERISTICS:
        (A) LENGTH: 17 base pairs
        (B) TYPE: nucleic acid

```
            (C) STRANDEDNESS: single
            (D) TOPOLOGY: linear (xi) SEQUENCE DESCRIPTION: SEQ ID NO:9:

GCCAGGACAC GGAGAGG                                                          17

(2) INFORMATION FOR SEQ ID NO:10:

(i) SEQUENCE CHARACTERISTICS:
            (A) LENGTH: 17 base pairs
            (B) TYPE: nucleic acid
            (C) STRANDEDNESS: single
            (D) TOPOLOGY: linear (xi) SEQUENCE DESCRIPTION: SEQ ID NO:10:

CCTCTCCCGC TCGCTCC                                                          17
```